United States Patent
Pfefferseder et al.

(10) Patent No.: US 7,276,912 B2
(45) Date of Patent: Oct. 2, 2007

(54) METHOD FOR THE OPERATION OF AN ANALYTICAL CIRCUIT FOR AN ELECTROMECHANICAL CELL

(75) Inventors: Anton Pfefferseder, Sauerlach-Arget (DE); Bernd Siber, Glonn (DE); Andreas Hensel, Egmating (DE); Ulrich Oppelt, Zorneding (DE)

(73) Assignee: Robert Bosch GmbH, Stuttgart (DE)

( * ) Notice: Subject to any disclaimer, the term of this patent is extended or adjusted under 35 U.S.C. 154(b) by 166 days.

(21) Appl. No.: 10/471,152

(22) PCT Filed: Jan. 19, 2002

(86) PCT No.: PCT/DE02/00163

§ 371 (c)(1),
(2), (4) Date: Jan. 2, 2004

(87) PCT Pub. No.: WO02/073182

PCT Pub. Date: Sep. 19, 2002

(65) Prior Publication Data

US 2004/0085073 A1    May 6, 2004

(30) Foreign Application Priority Data

Mar. 9, 2001    (DE)    ................... 101 11 264

(51) Int. Cl.
*G01N 27/28*    (2006.01)
(52) U.S. Cl. ..................... 324/450; 324/464
(58) Field of Classification Search ................ 324/450, 324/464; 205/775; 204/400, 401, 431
See application file for complete search history.

(56) References Cited

U.S. PATENT DOCUMENTS

| | | | |
|---|---|---|---|
| 4,556,472 A * | 12/1985 | Langdon ..................... | 204/406 |
| 4,735,691 A * | 4/1988 | Green et al. ............. | 205/779.5 |
| 5,522,980 A * | 6/1996 | Hobbs et al. ............... | 204/432 |
| 5,611,908 A * | 3/1997 | Matthiessen et al. ....... | 205/775 |
| 6,270,651 B1 * | 8/2001 | Essalik et al. .............. | 205/784 |
| 6,344,133 B1 * | 2/2002 | Formica et al. ............. | 205/775 |
| 7,169,358 B2 * | 1/2007 | Henkens et al. ........... | 422/68.1 |

FOREIGN PATENT DOCUMENTS

| | | |
|---|---|---|
| DE | 198 51 164 | 5/2000 |
| EP | 0 269 794 A | 6/1988 |
| EP | 0 417 347 A | 3/1991 |
| GB | 2 079 474 A | 1/1982 |
| GB | 2 176 296 A | 12/1986 |
| GB | 2 335 042 A | 9/1999 |
| GB | 2 343 518 A | 5/2000 |
| WO | 98 50789 A | 11/1998 |

\* cited by examiner

*Primary Examiner*—Vincent Q. Nguyen
(74) *Attorney, Agent, or Firm*—Michael J. Striker

(57) ABSTRACT

The invention proposes a method for operating an evaluation circuit for an electrochemical cell wherein the evaluation circuit is switched on for a first time period and is switched off for a second time period. The ratio between the first and the second time periods is selected to be less than 1. The measurement value of the electrochemical cell undergoes a current amplification in the evaluation circuit.

3 Claims, 3 Drawing Sheets

METHOD FOR THE OPERATION OF AN ANALYTICAL CIRCUIT FOR AN ELECTROMECHANICAL CELL

BACKGROUND OF THE INVENTION

The invention is based on a method for operating an evaluation circuit for an electrochemical cell according to the preamble to the independent claim.

The use of electrochemical cells as gas sensors is already known.

SUMMARY OF THE INVENTION

The method for operating an evaluation circuit for an electrochemical cell with the features of the independent claim has the advantage over the prior art that the evaluation circuit and therefore the electrochemical cell are operated in a pulsed fashion, where the time during which the evaluation circuit is switched off is longer than the time during which the evaluation circuit is switched on. This reduces power consumption, thus allowing a number of fire detectors, for example, to be connected to a single line, and also reduces the technical expense of producing an emergency power supply for the fire detectors. Pulsed operation of the evaluation circuit permits a high-consumption current amplifier to be attached, which can be produced more easily and inexpensively than a low-consumption current amplifier, since the power consumption can be comparatively high during times when the evaluation circuit is switched on, but is very low on average. Moreover, the mark-to-space ratio of the OFF time to the ON time increases the gas sensitivity for the electrochemical cell being used as a gas sensor.

Advantageous improvements of the method for operating an evaluation circuit for an electrochemical cell are possible by means of the steps taken and modifications included in the dependent claims.

It is particularly advantageous that the ON time is selected to be shorter than the discharge time so that after the device according to the invention is switched on, an equilibrium is established between the charge collected in the electrochemical cell during the OFF time and the charge flowing out of the electrochemical cell during the ON time. The OFF time here is selected so that the charge stored in the electrochemical cell is linearly proportional to the gas concentration.

It is also advantageous that there is a device for executing the method according to the invention, which is comprised of an electrochemical cell, an evaluation circuit with a current amplifier, and a switch that serves to switch on and off the supply of power to the evaluation circuit. In one modification, the electrochemical cell also has a reference electrode, which is connected to a potentiostat that can be used to set a potential in the measuring electrode.

Finally, it is also advantageous that the method according to the invention and the device according to the invention can be used in a fire detector in which the electrochemical cell is used as a gas sensor for detecting fire gases.

BRIEF DESCRIPTION OF THE DRAWINGS

Exemplary embodiments of the invention are shown in the drawings and will be explained in detail in the subsequent description.

DETAILED DESCRIPTION OF THE PREFERRED EMBODIMENTS

Figure 1:
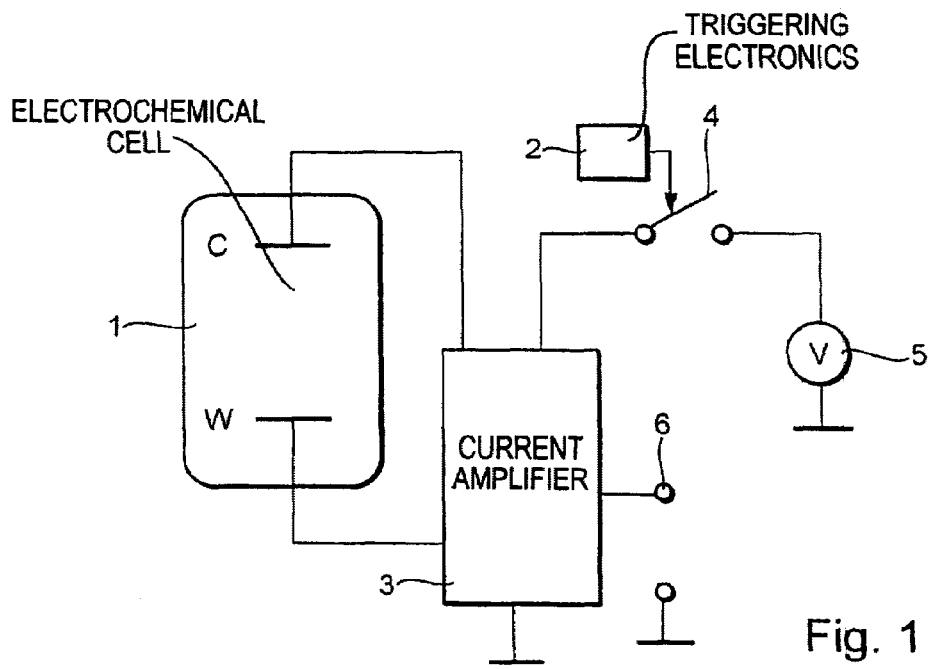
FIG. 1 shows a first block circuit diagram of the device according to the invention.

Electrochemical cells are sensors that can be used to determine the concentration of a gas in the air. These are sensors in which the gas to be detected triggers a chemical reaction in the sensor, thus generating an electrical current. The sensors, i.e. the electrochemical cells, have a measuring electrode and a counter electrode, which are used to detect the electrical current. The magnitude of the current I flowing between the measuring electrode and the counter electrode—which current is as a rule proportional to the gas concentration c ($I=e*c$, where e represents the gas sensitivity of the electrochemical cell, for example in nA/ppm)—can be used to determine the gas concentration. There are also embodiments of electrochemical cells that are additionally equipped with a reference electrode, which can be used to stabilize the potential of the measuring electrode or to set a particular potential in the measuring electrode. The setting of a particular potential difference between the measuring electrode and the counter electrode can, for example, be necessary in order to sense particular types of gas, since the sensitivity to a type of gas can depend, among other things, on the potential difference.

If a reference electrode is used, then the reference electrode is connected to an input of a potentiostat and the output of the potentiostat is connected to the counter electrode of the electrochemical cell. The output of the potentiostat then influences the counter electrode, causing the desired potential to be set in the measuring electrode. However, if only two electrodes are used, i.e. the measuring electrode and the counter electrode, then only one current amplifier is required in the electrical evaluation circuit.

If the electrochemical cell is disconnected from the evaluation circuit, then the current generated by the electrochemical cell can no longer flow. The same thing happens if the evaluation circuit is disconnected from the power supply and receives high-impedance inputs while in the OFF state. In both cases, the electrochemical cell begins to polarize, i.e. a voltage develops between the measuring electrode and the counter electrode. When the electrochemical cell is reconnected to the evaluation circuit or the power supply is switched on again, the charge stored in the electrochemical cell must first flow out via the current amplifier before the evaluation circuit generates a signal that corresponds to the gas concentration. This means that the evaluation circuit generates a signal that corresponds to the instantaneous gas concentration only a certain time after being switched on. Therefore, when using electrochemical cells that must measure a gas concentration over a long time period at a high sampling rate, the evaluation circuit is usually supplied with power in an uninterrupted fashion.

Electrochemical cells can, for example, be used to detect fire gases as part of a fire detector. This particular use requires the evaluation circuit to have a very low power consumption. The invention will now propose a method for operating an evaluation circuit for an electrochemical cell, which has a low power consumption in the evaluation circuit. To that end, the evaluation circuit is periodically switched off for a time period Ta and is switched on for a time period Te. This reduces the power consumption of the circuit by the mark-to-space ratio of Te divided by Ta. This takes advantage of the fact that the electrochemical cell stores the charge quantity generated by the chemical reaction when this charge cannot flow out via a measuring electrode and a counter electrode. If the evaluation circuit is switched off for the time period Ta, then the charge stored in the electrochemical cell during this time period is proportional to the gas concentration and to the OFF time Ta:

$$Q1 = e*c*Ta$$

This is only true if the OFF time is selected to be short enough that the polarization voltage generated, which can influence the gas sensitivity of the electrochemical cell, remains low. When the evaluation circuit is switched on again, if the time constant of the discharge process is greater than the ON time, then the charge $$Q2 = I*Te$$

flows during the ON time Te.

If the switching on and switching off are repeated periodically, then the polarization voltage of the electrochemical cell is increased until the charge quantity flowing out while the evaluation circuit is switched on is equal to the charge quantity generated while the evaluation circuit is switched off. At equilibrium, therefore, when the evaluation circuit is switched on, a current of the magnitude:

$$I = e*c*Ta/Te$$

flows. The concentration of the gas to be detected can then be determined by measuring this current. In addition to the low power consumption, therefore, another advantage of the method according to the invention is that the gas sensitivity of the electrochemical cell is increased by the mark-to-space ratio Ta/Te.

FIG. 1 shows a first block circuit diagram of the device according to the invention. An electrochemical cell has a counter electrode C and a measuring electrode W. The electrochemical cell 1 is connected via the electrodes C and W to inputs of a current amplifier 3. On the one side of its power supply connections, the current amplifier 3 is connected to ground and on the other side, it is connected to a switch 4. Triggering electronics 2 close the switch 4 for the ON time Te and open it for the OFF time Ta.

On the other side, the switch 4 is connected to a power supply 5, the other side of which is in turn is connected to ground. Either a current or a voltage that is characteristic of the gas concentration can be detected from the signal output of the current amplifier 3, which is labeled with the reference numeral 6. In a manner not shown here, the triggering electronics 2 are permanently connected to the power supply 5 in order to execute the periodic switching on and off of the switch 4. In this instance, the switch 4 is a transistor switch, but it is also possible for other switches to be used.

Figure 2:
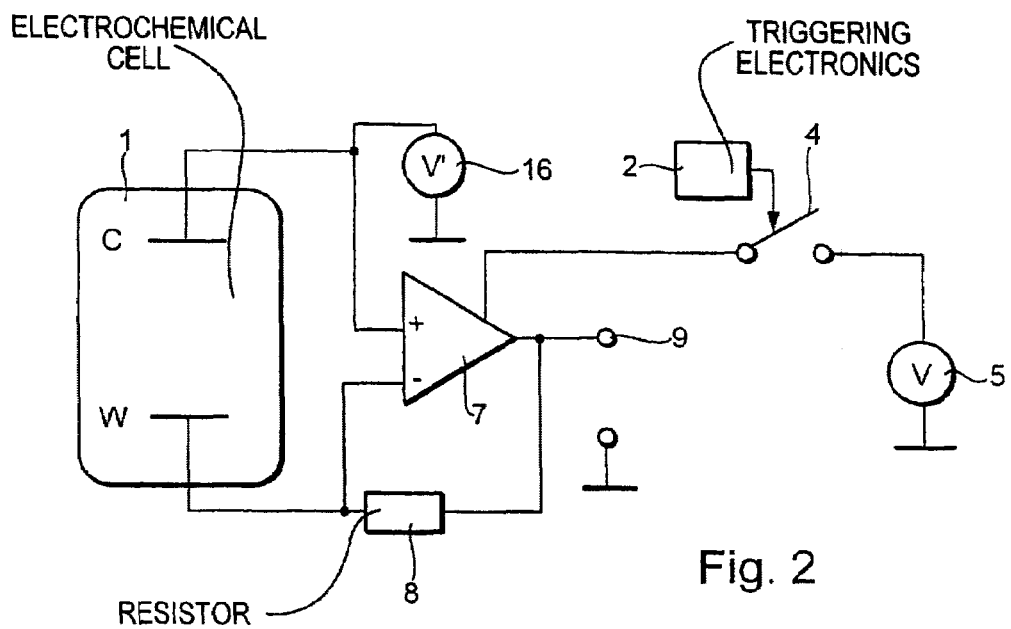
FIG. 2 shows a second block circuit diagram of the device according to the invention.

FIG. 2 shows a second block circuit diagram of the device according to the invention. The electrochemical cell 1 is connected via the counter electrode C to a positive input of an operational amplifier 7 and is connected via the measuring electrode W to the negative input of the operational amplifier 7. The positive input of the operational amplifier 7 is also connected to a reference voltage V' 16. In general, V'=0V (ground) is selected as the reference voltage. However, V' can also be set to a value of greater than 0V in order to permit compensation for offset currents of the electrochemical cell. In electrochemical cells, offset currents can occur in both current directions.

The measuring electrode W is also connected to a resistor 8. The operational amplifier 7 here is operated as a current amplifier. On its other side, the resistor 8 is connected to an output of the operational amplifier 7. An output electrode 9 is provided there, at which the amplified voltage or amplified current can be picked up. One power supply connection of the operational amplifier 7 is connected to ground, while the other is connected to the switch 4, which is triggered by the triggering electronics 2. This current amplifier circuit can also be operated with a symmetrical power supply.

The power supply 5 is situated on the other side of the switch 4 and is itself connected to ground on its other side.

Figure 3:
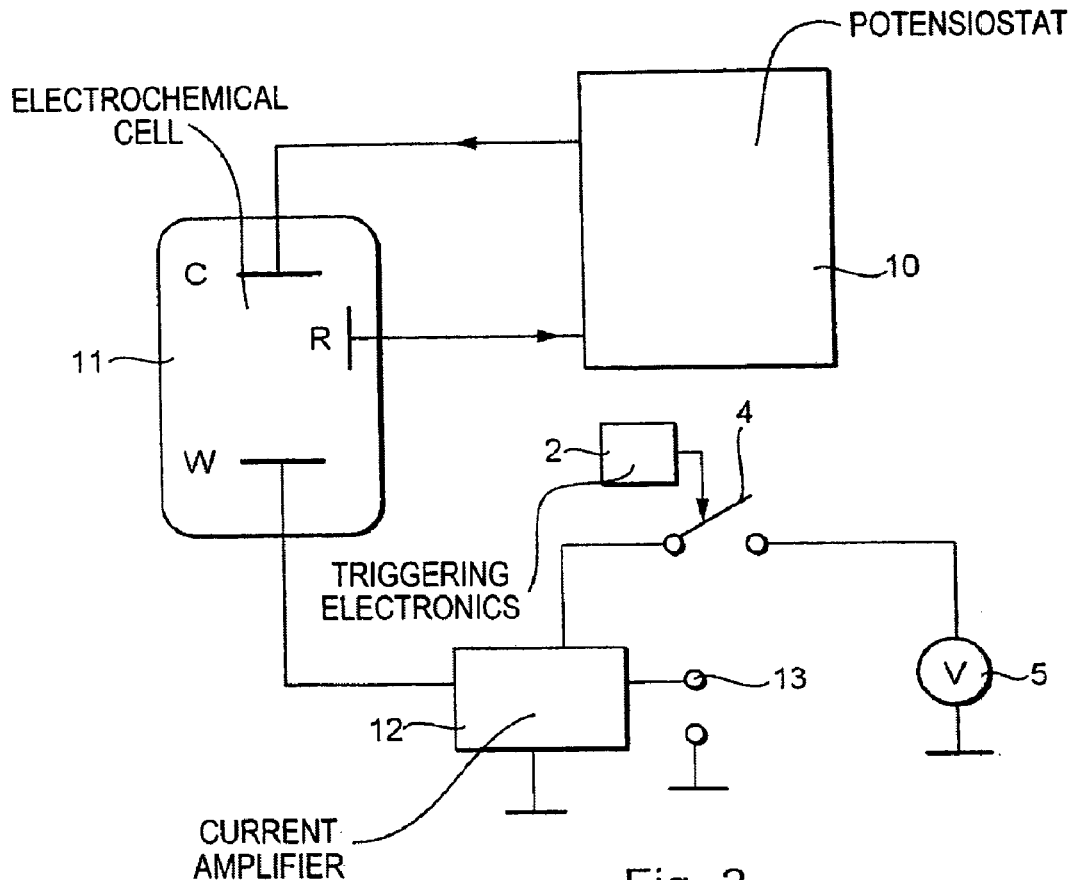
FIG. 3 shows a third block circuit diagram of the device according to the invention.

FIG. 3 shows a third block circuit diagram of the device according to the invention. An electrochemical cell 11 has a counter electrode, which is connected to an output of a potentiostat 10. A reference electrode R is connected to an input of the potentiostat 10. A measuring electrode W is connected to an input of a current amplifier 12, whose signal output 13 is used to detect the amplified measurement signal. With respect to its supply voltage, the current amplifier 12 is connected to ground on the one hand, and to the switch 4 on the other, which is in turn connected on its other side to the power supply 5, which is in turn connected to ground. The triggering electronics 2 trigger the switch 4.

Figure 4:
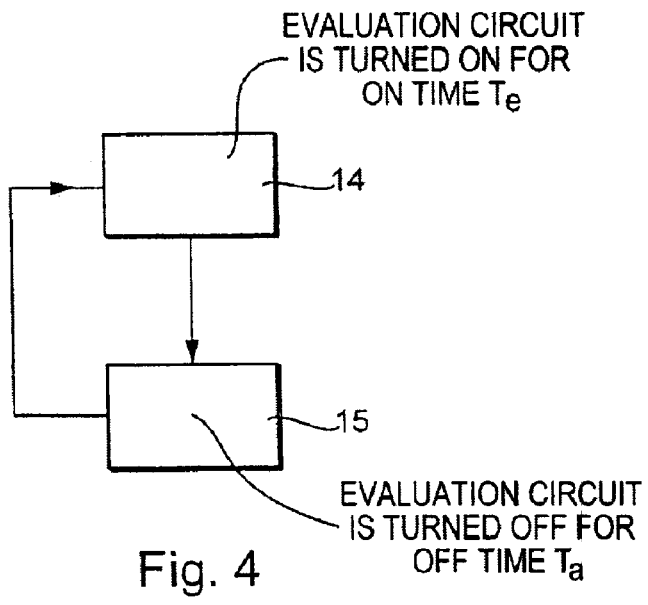
FIG. 4 shows a flowchart of the method according to the invention.

FIG. 4 shows the method according to the invention in the form of a flowchart. The triggering electronics 2, which include the power supply 5, close the switch 4; as a result, the switch 4 turns on the evaluation circuit, which includes the current amplifier 3 or 12, for the ON time Te. This ON time lasts 9 ms in this instance. After the ON time Te has elapsed, the power supply 5 is switched off due to the opening of the switch 4, for the OFF time Ta. The OFF time Ta is longer than the ON time Te. This occurs periodically.

Figure 5:
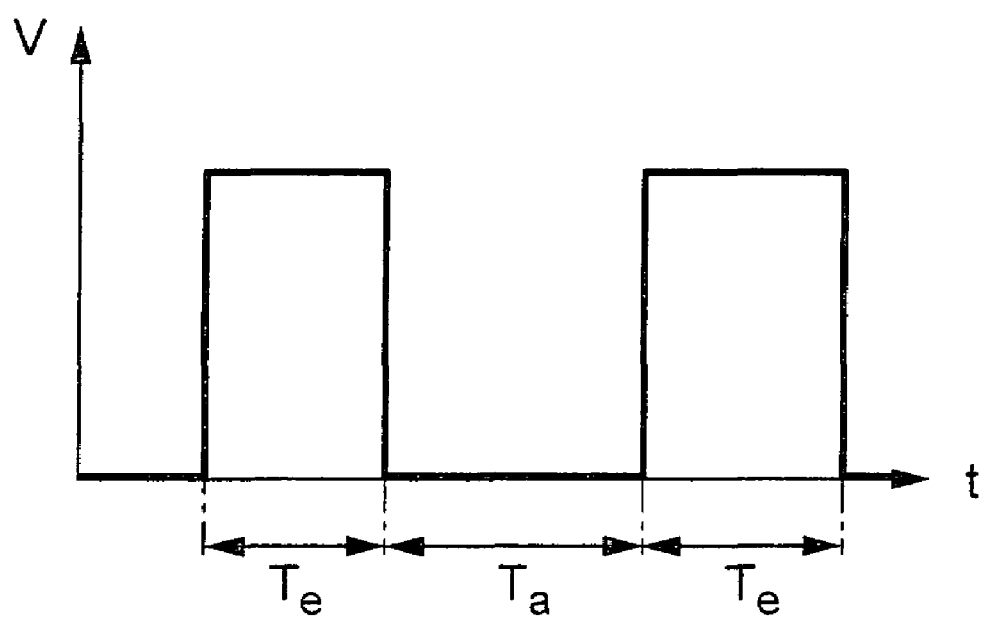
FIG. 5 shows a voltage/time graph of the supply voltage of the evaluation circuit.

FIG. 5 depicts the supply voltage present in the current amplifier 3 in the form of a voltage/time graph. The supply voltage is switched on for the time period Te and then switched off for the time period Ta. This repeats periodically.

The invention claimed is:

1. A method for operating an evaluation circuit (3) for an electrochemical cell (1), characterized in that the evaluation circuit (3) is switched on for a first time period (Te) and is switched off for a second time period (Ta), wherein the ratio between the first and second time periods is selected to be less than one, wherein a concentration of a gas to be detected is determined periodically when the evaluation circuit is switched on during the first time period (Te), wherein the first time period (Te) is selected so that the first time period (Te) is shorter than the discharge time constant of the electrochemical cell.

2. A method for operating an evaluation circuit (3) for an electrochemical cell (1), characterized in that the evaluation circuit (3) is switched on for a first time period (Te) and is switched off for a second time period (Ta), wherein the ratio between the first and second time periods is selected to be less than one, wherein a concentration of a gas to be detected is determined periodically when the evaluation circuit is switched on during the first time period (Te), wherein the second time period (Ta) is selected to produce a linear proportionality between a gas concentration that the electrochemical cell measures and a current that the electrochemical cell generates.

3. A device for operating an evaluation circuit (3) for an electrochemical cell (1), switched on for a first time period (Te) and switched off for a second time period (Ta) with a ratio between the first and second time periods selected to be less than one, a concentration of a gas to be detected periodically determined, and the evaluation circuit switched on for the first time period (Te), wherein the electrochemical cell (1) is connected to the evaluation circuit (3), and the evaluation circuit has a current amplifier and a switch (4) that periodically switches on the power supply (5) of the evaluation circuit for the first time period (Te) and switches it off for the second time period (Ta), wherein the electrochemical cell (1) has a reference electrode (R), which is triggered by a potentiostat (10) in order to set a potential in a measuring electrode of an electrochemical cell (11).

* * * * *